United States Patent [19]

Draeger et al.

[11] Patent Number: 4,786,591
[45] Date of Patent: Nov. 22, 1988

[54] PROCESS FOR DETERMINING THE BINDING CAPACITY OF THYROXIN-BINDING GLOBULIN

[75] Inventors: Brigitte Draeger, Tutzing; Winfried Albert, Pähl; Martina Junius, Bernried; Jürgen Rasch, Tutzing, all of Fed. Rep. of Germany

[73] Assignee: Boehringer Mannheim GmbH, Mannheim, Fed. Rep. of Germany

[21] Appl. No.: 945,785

[22] Filed: Dec. 23, 1986

Related U.S. Application Data

[63] Continuation-in-part of Ser. No. 827,349, Feb. 7, 1986, abandoned.

[30] Foreign Application Priority Data

Dec. 24, 1985 [DE] Fed. Rep. of Germany ....... 3546014

[51] Int. Cl.$^4$ .................. G01N 33/53; G01N 33/543; G01N 33/549
[52] U.S. Cl. ........................................ 435/7; 436/500; 436/512; 436/518; 436/532; 436/548; 436/817
[58] Field of Search ............... 436/512, 500, 532, 548, 436/518, 817; 435/7

[56] References Cited

U.S. PATENT DOCUMENTS

| | | | |
|---|---|---|---|
| Re. 32,098 | 6/1972 | Chopra | 424/1 |
| 4,366,143 | 9/1980 | Midgley et al. | 436/501 |
| 4,410,633 | 9/1980 | Hertl et al. | 436/500 |
| 4,467,030 | 8/1984 | Kleinhammer et al. | 435/7 |
| 4,476,228 | 11/1982 | Huchzermeier et al. | 436/500 |
| 4,481,298 | 11/1984 | Cone et al. | 436/500 |
| 4,636,478 | 1/1987 | Siebert et al. | 436/518 |

OTHER PUBLICATIONS

The Merck Manual, 14th edition (1982), pp. 997–1000.
Diagnostic Tests Handbook (1986), p. 143, publisher Keith Lassner, editor Regina Daley Ford.
Alberts et al., Molecular Biology of the Cell, published by Garland Publishing Inc., 1983, pp. 958–959.
Alberts et al., Molecular Biology of the Cell, published by Garland Publishing Inc., 1983, p. 966.

Primary Examiner—Robert J. Warden
Assistant Examiner—Florina B. Hoffer
Attorney, Agent, or Firm—Felfe & Lynch

[57] ABSTRACT

The present invention provides a process for determining the binding capacity of thyroxin-binding globulin (TBG) according to the principle of heterogeneous enzyme immunoassay, wherein the serum sample to be investigated is incubated with enzyme-labelled $T_4$ or $T_3$ and immobilized antibody against TBG or $T_4$, the phase are separated and the labelling enzyme is measured in one of the phases.

13 Claims, 3 Drawing Sheets

PROCESS FOR DETERMINING THE BINDING CAPACITY OF THYROXIN-BINDING GLOBULIN

This application is a continuation-in-part of application Ser. No. 827,349, filed Feb. 7, 1986, now abandoned.

The present invention is concerned with a heterogeneous process for the determination of the binding capacity of thyroxin-binding globulin (TBG), which is also called the T-uptake.

The thyroid hormone is present in the blood substantially in protein-bound form, thyroxin ($T_4$) thereby binding especially to the thyroxin-binding globulin (TBG). The determination of the binding capacity of TBG is of special importance in the scope of the diagnosis of the thyroid gland. Furthermore, in the preponderant number of cases, the product from the total $T_4$ concentration and 1/TBG correlate well with the $FT_4$ concentration (see L. R. Witherspoon, Journal of Clinical Immunoassay, 7/1984).

Known processes for the determination of the TBG binding capacity are described in Federal Republic of Germany Patent Specification No. 28 25 650. The disadvantage of the known processes is that it is necessary to use radioactive labellings and/or long periods of incubation, for example of 2 hours, have to be taken into account. The process of Federal Republic of Germany Patent Specification No. 28 25 560 also displays certain disadvantages which are due to the fact that it is a competitive process and not only $T_4$ but also $T_4$-enzyme conjugate have to be added.

Therefore, it is an object of the present invention to provide a process which does not proceed competitively, which does not require radioactive material, only needs short times and, in the case of a simple carrying out of the test, displays a high degree of exactitude. Furthermore, it is an object of the present invention to provide a process for the preparation of a control or standard solution suitable for the process according to the present invention.

Thus, according to the present invention, there is provided a process for determining the binding capacity of the thyroxin-binding globulin (TBG) according to the principle of heterogeneous enzyme immunoassay, wherein the serum sample to be investigated is incubated with enzyme-labelled $T_4$ or $T_3$ and immobilised antibody against TBG or $T_4$, the phases are separated and the labelling enzyme is measured in one of the phases.

In the case of a most simple carrying out of the test, the process according to the present invention can be performed with an incubation time of at most 15 minutes.

In contradistinction to all known heterogeneous processes for the determination of the binding capacity of TBG, which are carried out with immobilised anti-$T_4$ antibodies so that, in the carrying out thereof, TBG or anti-$T_4$ antibodies compete for the $T_4$ or a $T_4$ conjugate, the preferred embodiment of the process according to the present invention is carried out with immobilised anti-TBG antibodies. It is also to be regarded as being very surprising that, in the case of the process according to the present invention, exact results are obtained since the art teaches that enzyme-labelled $T_3$ or $T_4$ is not bound by serum proteins (TBG). The processes described in French Patent Specification No. 81.17997 and in Federal Republic of Germany Patent Specification No. 28 25 650 depend upon these special properties.

As enzyme labellings for the $T_3$ or $T_4$, there can, within the scope of the present invention, be used all enzymes which are suitable for this purpose and which can easily be determined, such as are well known to the expert, preferred examples therefor including peroxidase and $\beta$-galactosidase. The enzyme is preferably coupled via a spacer to the hormone, the length of the spacer being 3 to 8 carbon atoms and preferably 4 or 5 carbon atoms. The coupling can take place, for example, via an active ester of the hormone or of the hormone derivative. As spacers for the connection of $T_4$ or $T_3$ and the labelling enzyme, it is especially preferred to use aminobutyric acid or glycylglycine, preferably in the form of their hydroxysuccinimide esters.

The enzyme-labelled $T_4$ or $T_3$, which is hereinafter referred to as conjugate, is, in the case of the process according to the present invention, employed in such a concentration that $T_4$ is not markedly removed from the TBG-$T_4$ complex present in the serum. Therefore, the conjugate is preferably used in an insufficient amount in comparison with the TBG total concentration to be expected.

As conjugate there is preferably used one in which the molecular ratio of $T_4$ or $T_3$ to the labelling enzyme, especially $\beta$-galactosidase, is from 1 to 5:1.

Because of its greater binding capacity, in the case of the process according to the present invention, it is preferred to operate with a $T_4$-containing conjugate which leads to a better sensitivity. However, the process can also be carried out in the same way with $T_3$ conjugate.

As anti-TBG antibody, there can be used a polyclonal as well as a monoclonal antibody, the latter being preferred, or a fragment of such an antibody. The immobilisation of the antibody can take place in known manner such that the antibody is bound directly on to the carrier or, with the utilisation of its immunological binding ability, is fixed via an immobilised anti-antibody or a fragment thereof. The immobilisation of the anti-TBG antibody via an anti-antibody bound to the solid phase or a fragment thereof has the great advantage that the valuable anti-TBG antibody is actively bound practically to an extent of 100% and thus can be used in a smaller amount than in the case of direct fixing, which always involves a certain loss of activity.

Especially preferred is an embodiment in which there is used an immobilised antibody directed against the Fc part of the anti-TBG antibody which is reacted with the dissolved anti-TBG antibody, with fixing of the latter. The above statements apply analogously when, instead of anti-TBG antibody, there is used anti-$T_4$ antibody.

The process according to the present invention can be carried out in two states in which, in the first state, the sample is incubated with the conjugate and, in the second stage, is then incubated with the immobilised antibody against TBG or $T_4$. Insofar as anti-$T_4$ antibodies are hereby used, the second incubation is preferably carried out for no longer than 5 minutes and preferably for 0.5 to 2 minutes. In the case of the period of the second incubation going beyond this, competitive reactions can occur which reduce the exactitude.

In the case of the use of antibodies against TBG, the process can preferably also be carried out in one stage in such a manner that all components, including the solid phase, are mixed together simultaneously.

The present invention also provides a process for the determination in serum of the binding capacity of the thyroxin-binding globulin (TBG) according to the principle of heterogeneous enzyme immunoassay, in which the serum sample to be investigated is incubated with enzyme-labelled $T_3$ or $T_4$ and immobilised antibody against TBG or $T_4$, the phases are separated and the labelling enzyme is measured in one of the phases, wherein, for the control, instead of the serum sample there is used a control or standard human serum which contains monoclonal anti-$T_4$-antibodies in a definite amount.

An advantage of this process according to the present invention is that no TBG is necessary for the production of a calibration curve.

In the process for the determination of the binding capacity of the thyroxin-binding globulin (TBG) in serum according to the principle of heterogeneous enzyme immunoassay, the amount of TBG free of $T_3$ and $T_4$ is determined via the amount of fixed or non-fixed enzyme-labelled thyroxin.

For this purpose, it is necessary to produce a calibration curve in which the uptake value is plotted against the content of enzyme. In this case, according to the principle of heterogeneous enzyme immunoassay, samples with enzyme-labelled thyroxin ($T_4$) or triiodothyronin ($T_3$) and immobilised antibodies against TBG or $T_4$ are incubated which, instead of the sample to be investigated, contain a control or standard human serum which contains a definite amount of monoclonal anti-$T_4$-antibodies.

In a preferred embodiment of the process according to the present invention, the control or standard human serum containing the monoclonal anti-$T_4$-antibodies is incubated with a definite amount of enzyme-labelled $T_4$ or $T_3$ and then brought into contact with a solid phase to which antibodies are bound which are directed against the Fc-$\gamma$ part of the monoclonal anti-$T_4$-antibody. Subsequently, the liquid phase is separated from the solid phase and the labelling enzyme contained in the liquid phase is measured in known manner. For this purpose, a $T_4$-$\beta$-galactosidase conjugate is especially preferably used.

The enzyme-labelled $T_4$ or $T_3$, hereinafter referred to as conjugate, is, in the case of this embodiment of the process according to the present invention, used in known concentration.

As anti-$T_4$-antibody, there is used a monoclonal antibody or a fragment of such an antibody. The immobilisation of the anti-$T_4$-antibody can take place in known manner, for example by binding the antibody directly to the carrier or, with utilisation of its immunological binding ability, via an immobilised anti-antibody or a fragment thereof. The immobilisation of the anti-$T_4$-antibody via an anti-antibody or a fragment thereof bound to the solid phase has the advantage that the anti-$T_4$-antibody is practically 100% actively bound and thus can be used in a smaller amount than in the case of direct fixing, which always involves a certain loss of activity.

In this case, an embodiment is especially preferred in which an antibody is used which is directed not only against the Fc part of the anti-TBG antibody but also against the Fc part of the anti-$T_4$-antibody.

The modified process according to the present invention can be carried out in two steps in which, in a first step, the control serum is incubated with the conjugate and, in a second step, is then incubated with the immobilised antibody against TBG or $T_4$. Insofar as anti-$T_4$-antibodies are hereby used, the second incubation is preferably carried out for not more than 5 minutes and preferably for 0.5 to 2 minutes. If the period of the second incubation is greater than this, competitive reactions can occur which reduce the exactitude.

The following Examples are given for the purpose of illustrating the present invention, reference thereby being made to the accompanying drawings, in which.

EXAMPLE 1

Figure 1:
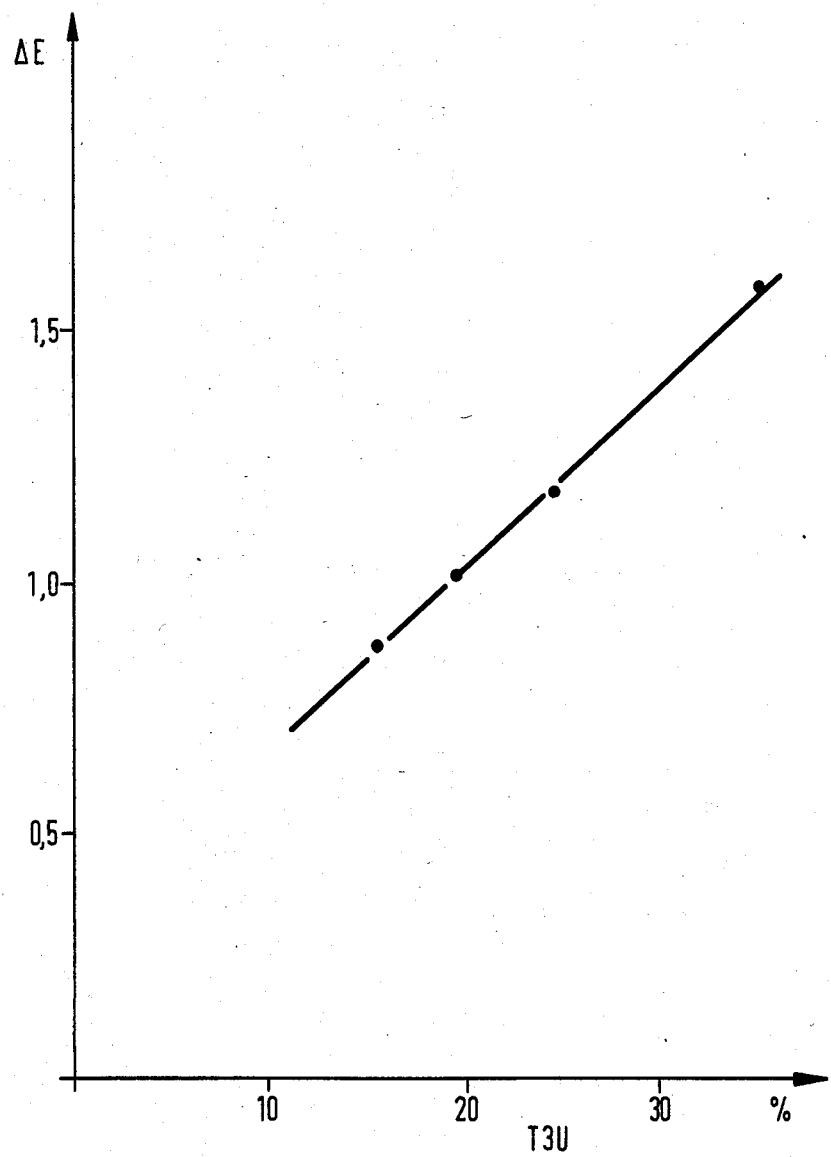
FIG. 1 is a calibration curve which was obtained with the process according to the present invention, using samples, the TBG binding capacity of which was known.

1. Reagents (a) Buffer:
100 mmol/liter hepes
2 mmol/liter magnesium aspartate
1% bovine serum albumen (BSA)
0.9% sodium chloride
0.2% surface-active agent (Tween),
pH=7.25 (37° C.).
(b) $T_4$-$\beta$-galactosidase
600 mU/ml. buffer
(c) monoclonal antibody (directed against TBG); 108 μg./ml. (The development of the monoclonal antibody took place according to the method of Kohler and Milstein (Eur. J. Immunol., 6, 292/1976, using TBG as immunogen).
(d) immobilised antibody (directed against the Fc part of the monoclonal antibody).

The antibody was obtained by immunising sheep with Fc parts of mouse immunoglobulins according to conventional processes. The antiserum was purified via ammonium sulphate precipitation and chromatography of DEAE-cellulose.

The fixing of the antibody on the filter paper took place according to the method described by P. Gemeiner and M. Pasteka (Applied Biochemistry and Biotechnology, 8, 381–393/1983) for the preparation of protein-cellulose conjugates by reductive alkylation of periodate-oxidised cellulose. There were provided 15 mg. purified antibody/g. of paper.

(e) chlorophenol red galactoside (CPRG) fleece:
0.25 μmol/5 mg. paper, prepared according to Federal Republic of Germany Patent Specification No. 33 45 748.

Carrying out of the test:
Serum was diluted in a volume ratio of 1:75 with the following mixture:
172 μl. buffer
30 μl. $T_4$-$\beta$-galactosidase solution
20 μl. MAB <TBG> solution (monoclonal antibody against TBG).

After incubating for 5 minutes at 37° C., 50 μl. of the mixture were allowed to be soaked up by 10 mg. of the coupling paper prepared according to (d) and was incubated for a further 5 minutes at 37° C. By means of subsequent centrifuging, the liquid which contains the unbound part of $T_4$-$\beta$-galactosidase was separated from the paper and passed over the chlorophenol red galactoside fleece and the enzyme kinetics were measured (mE/min) at 37° C. and 578 nm in a microcuvette with a filling volume of 27 μl. and a layer thickness of 0.6 cm.

The recalculation of the measurement signal into TBG binding values took place via a calibration curve which had been obtained with samples, the TBG values of which are known (FIG. 1).

Figure 2:
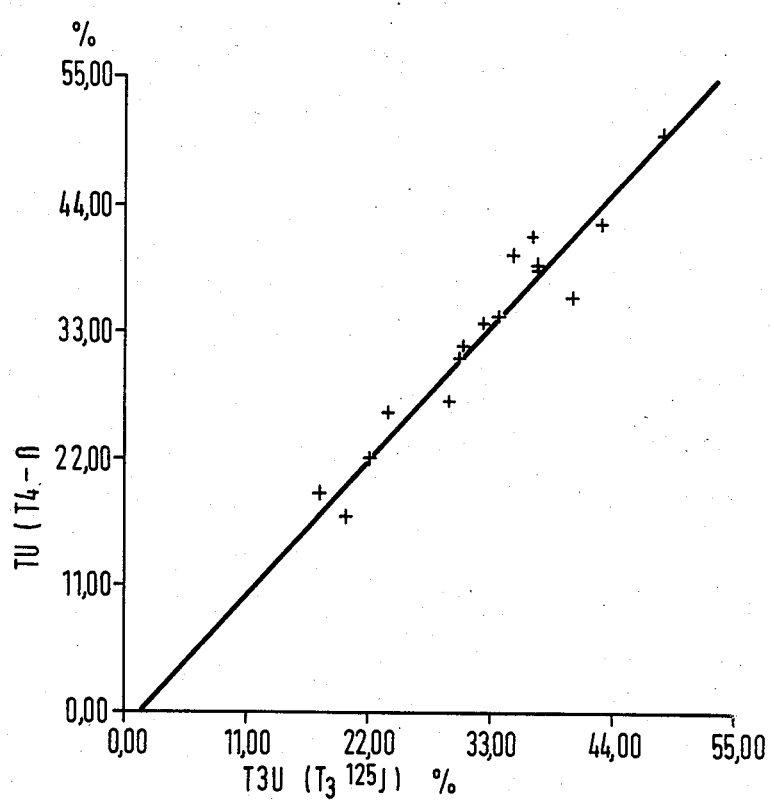
FIG. 2 is a comparison of the values obtained according to the present invention (ordinate) with the values of a known process (abscissa).

FIG. 2 shows a comparison of methods:

abscissa: Thyroxin binding capacity in serum (%) obtained with a radioassay ordinate: TBG binding capacity (%) obtained according to the Example standard main comp. analysis: Y−1.325+1.049×correlation coefficient: 0.964.

2. Preparation of the $T_4$-$\beta$-galactosidase conjugate with aminobutyric acid as spacer.

N-tert.-butoxycarbonyl-thyroxin (BOC-$T_4$) was prepared from thyroxin sodium salt and di-tert.-butyl dicarbonate analogously to the procedure described in European Patent Specification No. 01 08 400.

N-tert.-butoxycarbonyl-thyroxinyl-hydroxysuccinimide ester (BOC-$T_4$-OSu) was prepared from 0.5 mmol BOC-$T_4$, 3.6 mmol N-hydroxysuccinimide and 3.6 mmol dicyclohexyldiimide analogously to the procedure for the preparation of BOC-phenylalanine-OSu (Houben-Weyl, Methoden der organischen Chemie, Vol. XV/2, 74th year, p. 150).

The residue obtained after evaporation was dissolved in ethyl acetate and precipitated by the addition of petroleum ether.

N-tert.-butoxycarbonyl-thyroxinyl-aminobutyric acid-hydroxysuccinimide ester (BOC-$T_4$-Aba-OSu) was prepared in the following manner: To a solution of 0.5 g. BOC-$T_4$-OSu in 8 ml. dioxan was added dropwise a solution of 0.27 g. aminobutyric acid in 0.5 ml. 0.1M phosphate buffer (pH 8.5). After a reaction period of 2 hours, the reaction mixture was acidified and shaken out with ethyl acetate. The ethyl acetate phase was washed with water, dried and evaporated.

The residue was dissolved in 20 ml. ethylene glycol dimethyl ether and mixed with 0.07 g. N-hydroxysuccinimide and 0.12 g. dicyclohexylcarbodiimide. After a reaction time of 12 hours, it was filtered off, the solvent was evaporated, the residue was dissolved in ethyl acetate and the BOC-$T_4$-Aba-OSu was precipitated out with petroleum ether.

DC (HPTLC, RP 18; elution agent: nitromethane/ethanol 9:1 v/v)

$R_f$: 0.77; $^1$H-NMR (d$_6$-dimethylsulphoxide), δ(ppm): 1.32 (s, 9H), 1.77 (m, 4H), 2.80 (s, 4H), 7.03 (s, 2H), 7.79 (s, 2H).

15.8 mg. $\beta$-galactosidase were dissolved in 2.5 ml. 0.01M phosphate buffer (pH 7.0). While cooling with ice, 0.307 ml. of a 0.1% solution of BOC-$T_4$-Aba-OSu was slowly added thereto. The conjugate obtained was desalinated by gel filtration and purified by affinity chromatography over Spherosil-coupled TBG.

EXAMPLE 2

(a) Buffer: 110 mmol/l. hepes, 2.2 mmol/l. magnesium aspartate, 1% BSA, 0.9% sodium chloride, 0.2% Tween; pH=7.25 (37° C.)

(b) $T_3$-$\beta$-galactosidase: 125 mU/ml. buffer (c) Antibodies directed against TBG immobilised on paper. The antibodies were obtained by immunisation of sheep with TBG according to conventional processes. The antibodies were, after ammonium sulphate precipitation and DEAE-cellulose chromatography, additionally purified immunosorptively over TBG coupled to Spherosil. The fixing of the antibody on to paper took place in the manner described in Example 1. There were provided 20 mg. purified antibody/g. of paper.

(d) Chlorophenol red galactoside solutions (5 mmol/l.) buffer: 100 mmol/l. hepes, 2 mmol/l. magnesium aspartate, 0.5% BSA, 0.9% sodium chloride, 0.2% Tween.

Carrying out of the test:

Serum was diluted with $T_3$-$\beta$-galactosidase solution in a volume ratio of 1:10. 50 μl. of this mixture were absorbed on to 10 mg. of the TBG-antibody-carrying paper and incubated for 10 minutes at 37° C. For the removal of non-bound $T_3$-$\beta$-galactosidase, the paper was washed three times with, in each case, 100 μl. buffer, whereby, after each washing step, the wash solution was removed by centrifuging. Subsequently, the paper was impregnated with 50 μl. chlorophenol red galactoside solution. After incubating for 5 minutes at 37° C., the coloured material solution formed was separated from the paper by centrifuging and measured in a microcuvette with a filling volume of 27 μl. and a layer thickness of 0.6 cm. at a wavelength of 578 nm.

The extinction measured is proportional to the binding capacity of the sample.

| sample | $\Delta E_{578\ nm}$ (referred to a layer thickness of 1 cm.) |
|---|---|
| serum with low binding capacity | 357 mU |
| T3U (radioassay): 59% | |
| TBG <2 μg./ml. | |
| serum with normal binding capacity | 1351 mU |
| T3U: 28% | |
| TBC: 16 μg./ml. | |

Preparation of the $T_3$-$\beta$-galactosidase conjugate.

The preparation of the N-tert.-butoxycarbonyltriiodothyronine (BOC-$T_3$) and of the N-tert.-butoxycarbonyltriiodothyronine hydroxysuccinimide ester (BOC-$T_3$-OSu) took place in a manner analogous to that described in Example 1.

BOC-$T_3$-OSu: DC (HPTLC, RP 18, elution agent: nitromethane/ethanol 9:1 v/v) $R_f$=0.6

The reaction of the $\beta$-galactosidase with BOC-$T_3$-Osu and the subsequent purification was also carried out as described in Example 1.

EXAMPLE 3

Reagents:

(a) Buffer: 100 mmol/l. hepes, 2 mmol/l. magnesium aspartate, 1% BSA, 0.9% sodium chloride, 0.2% Tween (pH 7.25 (37° C.)

(b) $T_4$-$\beta$-galactosidase: 170 mU/ml. buffer (prepared as in Example 1)

(c) anti-$T_4$-antibody immobilised on paper (S <$T_4$> paper).

The antibodies were obtained by conventional processes by the immunisation of sheep with $T_4$ which was bound via glutardialdehyde to bovine serum albumin.

The antiserum was purified via ammonium sulphate precipitation and chromatography on DEAE-cellulose.

The fixing of the antibody on to paper took place analogously to the method described in Example 1.

There were used 10 mg. purified antibody/g. of paper.

(d) Chlorophenol red galactoside (CPRG) fleece: 0.25 μmol/5 mg. of paper (as in Example 1).

Carrying out of the test:

Serum is diluted in a volume ratio of 1:20 with the following mixture:

140 μl. buffer (a)
50 μl. T$_4$-β-galactosidase solution (b)

After incubating for 5 minutes at 37° C., 50 μl. of the mixture were allowed to soak into 10 mg. of the S <T$_4$> paper (c) and incubation was continued for a further 5 minutes at 37° C. By means of subsequent centrifuging, the liquid, which contained the complexes of TBG and T$_4$-β-galactosidase, were separated from the paper, passed over the chlorophenol red galactoside fleece d) and the enzyme kinetics (mE/min.) measured at 37° C. and 578 nm in a microcuvette with a filling volume of 27 μl. and a layer thickness of 0.6 cm.

The recalculation of the measurement signal into T-uptake values took place via a calibration curve which had been obtained with samples, the uptake values of which were known.

The results thus obtained are set out in the following Table:

| serum | $\Delta E_{578\,nm}$, referred to layer thickness of 1 cm. | T-uptake % | T$_3$U (radio-assay) % | TBG (elisa) μg./ml. |
| --- | --- | --- | --- | --- |
| 1 | 665 mU | 42.3 | 40.1 | 5.6 |
| 2 | 1028 mU | 28 | 28.2 | 14.6 |
| 3 | 947 mU | 30.5 | 30.0 | 12.0 |
| 4 | 1129 mU | 25 | 18.3 | 18.6 |

EXAMPLE 4

A patient's serum sample or a plasma sample is diluted 1:75 with a 0.9% aqueous sodium chloride solution. The sample is thereafter pipetted into a test tube and tempered. Subsequently, there is added thereto a solution which contains buffer and stabiliser, this solution containing 55 mMole monosodium dihydrogen phosphate monohydrate and 1% bovine serum albumin, followed by incubation with a conjugate solution. The incubate solution contains 150 mMole hepes, 10 mMole magnesium aspartate and 1% bovine serum albumin, the pH thereof being 7.3. Furthermore, this solution contains a T$_4$-β-galactosidase conjugate and monoclonal antibodies against TBG. Incubation is carried out for 5 minutes, during which time the following immunological reaction takes place in homogeneous phase:

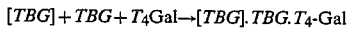

[TBG]+TBG+T$_4$Gal→[TBG].TBG.T$_4$-Gal

Subsequently, for the separation of the conjugate-antibody complex, there is added to the reaction solution an antibody which is directed against the Fc part of the monoclonal antibody. Incubation is carried out for 5 minutes, whereafter the liquid phase is separated off and mixed with chlorophenol red-galactoside. The fission of the substrate is then detected kinetically at λ=578 nm in a cuvette. The signal corrected by the adsorption at λ=700 nm is a measure of the T-uptake of the sample. The uptake value of a normal serum pool is thereby arbitrarily taken as TU=1.

A solution of T$_3$, T$_4$-antibodies is used as standard or control serum. The antibody is dissolved in 0.9% aqueous sodium chloride solution and subsequently the process is carried out in the manner described for the patient's serum. Various sera are prepared with different concentrations of monoclonal antibodies. The results obtained are set out in the following Table:

| MAB μg./test | mE/min. | T-uptake (%) |
| --- | --- | --- |
| 0.00 | 2430 | 85.5 |
| 0.14 | 984 | 29.2 |
| 0.28 | 718 | 19.6 |
| 0.56 | 528 | 12.3 |
| 1.12 | 431 | 8.6 |
| 1.68 | 387 | 6.9 |

EXAMPLE 5

Figure 3:
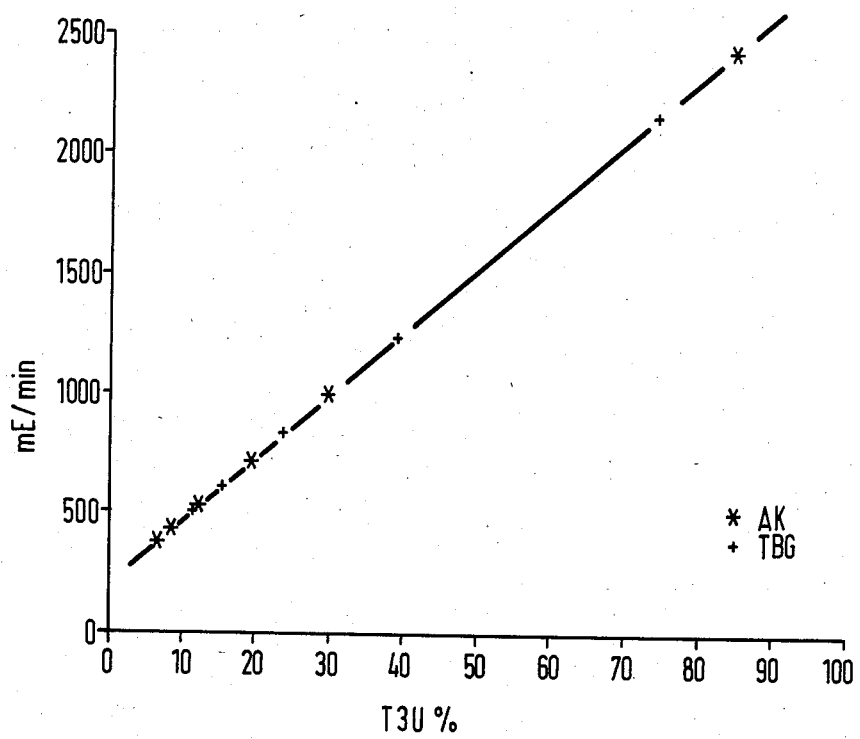
FIG. 3 is a calibration curve obtained using TBG standard and antibody standard.

The extent to which calibration curves produced according to the process of the present invention agree with calibration curves which have been produced with known amounts of TBG was examined. There was thereby obtained the calibration line shown in FIG. 3 of the accompanying drawings which is identical for the TBG standard and for the antibody standard.

We claim:

1. A process for determining the binding capacity of thyroxin binding globulin (TBG) comprising incubating a serum sample containing TBG with T$_4$ or T$_3$ bound via a spacer to an enzyme label and immobilized antibody which specifically binds to TBG under conditions favoring binding of TBG to labeled T$_4$ or T$_3$ and formation of complexes between said immobilized antibody and TBG bound to labeled T$_4$ or T$_3$, separating free and immobilized phrases and measuring label in one of the phases as a measurement of the binding capacity of thyroxin binding globulin in said sample.

2. A process for determining the binding capacity of thyroxin binding globulin (TBG) comprising incubating a serum sample containing TBG with T$_4$ bound via a spacer to an enzyme label without addition of unlabeled T$_4$ and with immobilized antibody which specifically binds to labeled T$_4$ unbound to TBG under conditions favoring binding of TBG to labeled T$_4$ and formation of complexes between labeled T$_4$ and said immobilized antibody, separating free and immobilized phases and measuring label in one of said phases as a measurement of the binding capacity of thyroxin binding globulin in said sample.

3. Process according to claim 1 or 2, wherein a spacer is used with a length of from 3 to 8 carbon atoms.

4. Process according to claim 3, wherein aminobutyric acid or glycylglycine is used as the spacer.

5. Process according to claim 1 or 2 comprising carrying out said process in two stages the first stage comprising incubating the sample with the enzyme labelled T$_3$ or T$_4$ and the second stage comprises incubating said sample and enzyme labelled T$_3$ or T$_4$ with the immobilized antibody against T$_4$ or TBG.

6. Process according to claim 5 wherein said immobilized antibody is an antibody against T$_4$ and the second incubation stage is carried out for not longer than 5 minutes.

7. Process according to claim 1 or 2, wherein said enzyme labelled T$_4$ is a T$_4$-β-galactosidase conjugate, the presence of which is determined in a color forming reaction.

8. A process for determining the binding capacity of thyroxin binding globulin (TBG) with T$_4$ or T$_3$ bound via a spacer to an enzyme, an antibody specific for TBG and an immobilized antibody which specifically binds to the Fc portion of said TBG specific antibody under conditions favoring binding of TBG to said labeled $T_4$ or $T_3$, said TBG specific antibody to TBG, and said immobilized Fc specific antibody to said TBG specific antibody, separating free and immobilized phases and measuring the label in one of said phases as a measure of the binding capacity of thyroxin binding globulin in said sample.

9. A process for determining the binding capacity of thyroxin binding globulin (TBG) comprising incubating a serum sample containing TBG with $T_4$ bound via a spacer to an enzyme, an antibody specific for labeled $T_4$ and an immobilized antibody which specifically binds to the Fc portion of said $T_4$ specific antibody under conditions favoring binding of $T_4$ to TBG, $T_4$ to said $T_4$ specific antibody and said immobilized Fc specific antibody to said $T_4$ specific antibody, separating free and immobilized phases and measuring the label in one of said phases as a measure of the binding capacity of thyroxin binding globulin in said sample.

10. Process according to claims 2, 8 or 9 wherein, the measurement obtained is compared to a control or standard which comprises human serum containing a known amount of monoclonal anti-$T_4$ antibodies.

11. Process according to claim 10 comprising incubating the control or standard human serum containing the monoclonal anti $T_4$-antibodies with a known amount of enzyme labelled $T_4$ or $T_3$ under conditions favoring formation of complexes between said antibodies and said $T_4$ or $T_3$, contacting said human serum containing labeled $T_4$ or $T_3$ with a solid phase to which are fixed antibodies which bind to Fc $\gamma$ part of the monoclonal anti-$T_4$-antibody under conditions favoring formation of complexes between said Fc $\gamma$ specific antibody and said monoclonal anti-$T_4$ antibody and separating the liquid phase from the solid phase and measuring the labelling enzyme contained in one of said phases.

12. Process according to claim 10 wherein said immobilized antibody specifically binds to a common epitope of said monoclonal anti-$T_4$ antibody and an anti-TBG antibody.

13. Process according to claim 8 or 9 wherein said antibody specific for TBG is a monoclonal antibody.

* * * * *